United States Patent
Moench et al.

(10) Patent No.: US 7,316,232 B2
(45) Date of Patent: Jan. 8, 2008

(54) DEVICE AND METHOD FOR SIMULTANEOUSLY DELIVERING BENEFICIAL AGENTS TO BOTH CERVICAL AND VAGINAL LUMEN SIDES OF A VAGINA

(75) Inventors: Thomas R. Moench, Baltimore, MD (US); Richard A. Cone, Baltimore, MD (US); Kevin J. Whaley, Baltimore, MD (US)

(73) Assignee: ReProtect, Inc., Baltimore, MD (US)

( * ) Notice: Subject to any disclaimer, the term of this patent is extended or adjusted under 35 U.S.C. 154(b) by 423 days.

(21) Appl. No.: 10/222,702

(22) Filed: Aug. 15, 2002

(65) Prior Publication Data

US 2003/0005937 A1 Jan. 9, 2003

Related U.S. Application Data

(63) Continuation of application No. 09/730,115, filed on Dec. 5, 2000, now Pat. No. 6,474,338, which is a continuation of application No. 09/187,940, filed on Nov. 6, 1998, now Pat. No. 6,216,697.

(60) Provisional application No. 60/064,903, filed on Nov. 7, 1997.

(51) Int. Cl.
*A61F 6/06* (2006.01)

(52) U.S. Cl. ........................ 128/830; 128/837

(58) Field of Classification Search ......... 128/830–841
See application file for complete search history.

(56) References Cited

U.S. PATENT DOCUMENTS

| | | | | |
|---|---|---|---|---|
| 2,157,689 A | * | 5/1939 | Clark, Jr. | 128/837 |
| 3,042,029 A | * | 7/1962 | Johansson | 128/837 |
| 4,200,090 A | | 4/1980 | Drobish | |
| 4,630,602 A | * | 12/1986 | Strickman et al. | 128/837 |
| 4,785,804 A | * | 11/1988 | Tlapek et al. | 128/841 |
| 4,795,425 A | * | 1/1989 | Pugh | 128/844 |
| 4,862,899 A | * | 9/1989 | Bucaro | 600/562 |
| 5,207,232 A | * | 5/1993 | Shihata | 128/837 |
| 5,228,456 A | * | 7/1993 | Karg et al. | 128/837 |
| 5,295,984 A | * | 3/1994 | Contente et al. | 604/317 |
| 5,592,949 A | | 1/1997 | Moench et al. | |
| 6,241,846 B1 | | 6/2001 | Contente et al. | |
| 6,264,638 B1 | | 7/2001 | Contente | |

FOREIGN PATENT DOCUMENTS

| | | |
|---|---|---|
| DE | 511832 | 10/1930 |
| EP | 0 006 609 | 1/1980 |

* cited by examiner

*Primary Examiner*—Michael A. Brown
(74) *Attorney, Agent, or Firm*—Bell, Boyd & Lloyd LLP

(57) ABSTRACT

The present invention reveals a device, a kit and a method for simultaneously delivering and distributing at least one beneficial agent to both the cervical and vaginal lumen sides of a vagina. The device is made of a flexible circular rim and a flexible dome. The device can exist in either a relaxed state or in a compressed state. In the compressed state, pouches are formed for carrying and delivering the beneficial agent to both the cervical and vaginal lumen sides of the vagina.

39 Claims, 3 Drawing Sheets

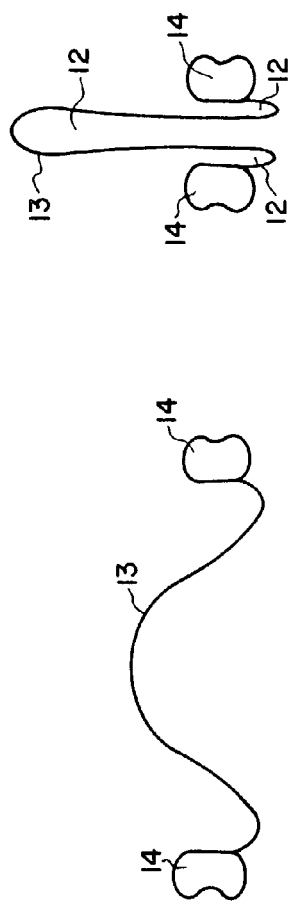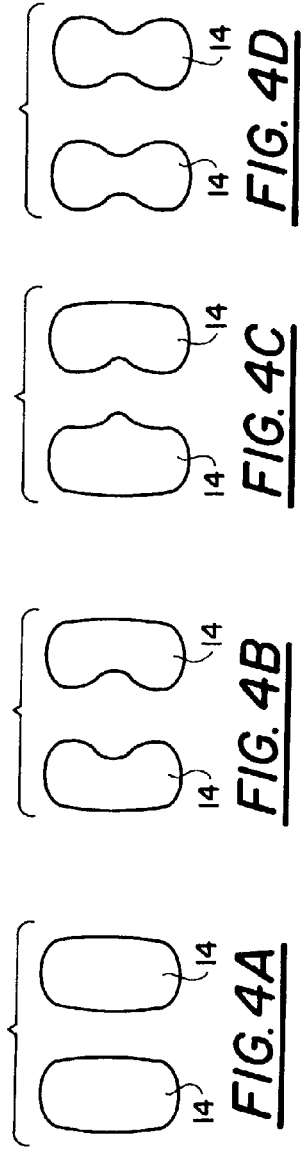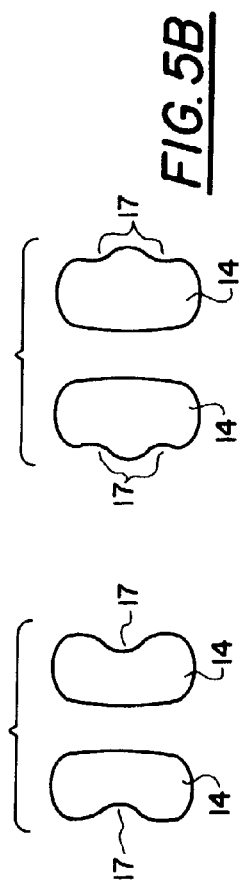

FIG. 6A
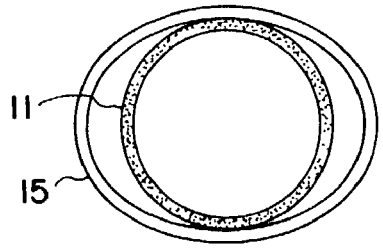
FIG. 6C
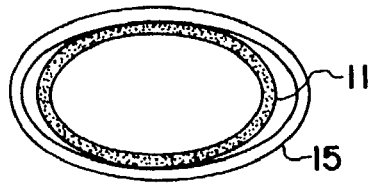
FIG. 6B
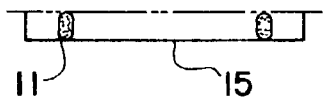
FIG. 6D
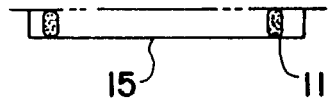
LATERAL COMPRESSION MAKES RIM
ARC SLIGHTLY DOWNWARD
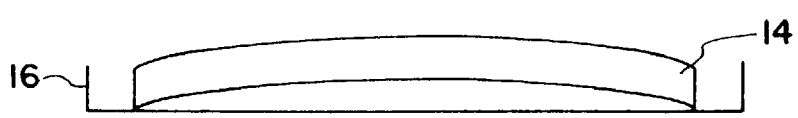
FIG. 7A
DOWNWARD PRESSURE FLATTENS
COMPRESSED RIM AGAINST PACKAGE TRAY
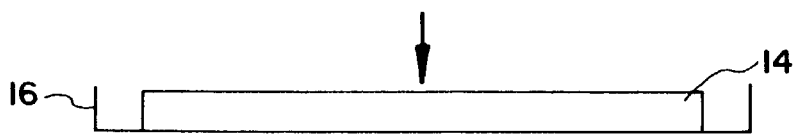
FIG. 7B

DEVICE AND METHOD FOR SIMULTANEOUSLY DELIVERING BENEFICIAL AGENTS TO BOTH CERVICAL AND VAGINAL LUMEN SIDES OF A VAGINA

PRIORITY CLAIM

This application is a continuation of and claims the benefit of U.S. patent application Ser. No. 09/730,115, filed Dec. 5, 2000, now issued as U.S. Pat. No. 6,474,338, which is a continuation of U.S. patent application Ser. No. 09/187,940, filed Nov. 6, 1998, now issued as U.S. Pat. No. 6,216,697, which claims the benefit of U.S. Provisional Patent Application 60/064,903, filed Nov. 7, 1997, the contents of each are incorporated herein by reference in their entirety.

BACKGROUND OF THE INVENTION

1. Field of the Invention

The present invention discloses a device, a kit and a method for simultaneously delivering at least one beneficial agent to both the cervical and vaginal lumen sides of a vagina. The device is made of a flexible circular rim and a flexible dome. The device can exist in either a relaxed state or in a compressed state. In the compressed state, multiple pouches are formed for carrying and delivering the beneficial agent to both the cervical and vaginal lumen sides of the vagina.

2. Description of the Related Art

Beneficial agents are defined herein as a medicinal component or components to be delivered to the female genital tract. Such beneficial agents include spermicides, bactericides, viricides, fungicides, anti-protozoal agents, hormones, nucleic acids, proteins, enzymes, vaccinogens, antibodies or cytokines, peptides, metal chelators, buffers and the like. Thus, beneficial agents as used herein include protective agents and treating agents and are sometimes referred to herein simply as the agent or agents.

There is a need for a vaginal device that can deliver substantial volumes of a beneficial agent in the form of a gel, cream, lotion, powder or other form, and distribute the agent(s) to all regions of the female genital tract, including the introitus, vagina and cervix, while providing a mechanical barrier that covers the cervix (see FIG. 1). Current devices are not well suited for this task.

Contraceptive diaphragms, for example, the Ortho ALL-FLEX® diaphragm, and related devices easily contain on their concave surface, and deliver to the cervical region of the vagina, substantial volumes (up to 10 ml) of contraceptive spermicides (see FIGS. 1 and 2). An agent applied to this concave surface is not wiped off during insertion into the vagina since compression of the diaphragm in preparation for insertion surrounds the spermicide fully in an enclosed pouch in the interior of the compressed diaphragm.

However, contraceptive diaphragms and related devices are poorly suited for delivering spermicides and other beneficial agents to the rest of the vagina, the vaginal lumen side of the device, the region directly exposed to ejaculated semen. If an agent is applied to the diaphragm's convex surface, much of the agent is "wiped off" by the vaginal introitus as the diaphragm is being inserted (see FIGS. 1 and 2). The tone of the circumvaginal muscle located just inside the introitus enhances this wiping off action by constricting the vaginal barrel. Also, since this circumvaginal muscle tone is highly variable between individual women, it not only limits delivery of an agent on this side of a diaphragm, but causes potentially wide variations of the dose of a beneficial agent actually delivered to the non-cervical region of the vagina.

Cervical caps suffer limitations similar to those of diaphragms. Vaginal sponges can prevent the wipe-off problem, but do not form secure cervical barriers, and sponges may be felt, particularly by the male partner during intercourse as obstructions of the vaginal barrel. A device known as FemCap™ allows better delivery of agent on both sides than most of these other devices. However, FemCap™ sequesters a large portion of the agent applied to the non-cervical side of the vagina in a rather inaccessible crevice, limiting the agent's distribution to the vaginal mucosa. Moreover, unlike the present invention, FemCap™ does not extend upon insertion to distribute the agent over a wide area.

The need to deliver beneficial agents to the cervical side of the vagina is obvious when the goal is contraception, holding a spermicide near the cervix places the spermicide in excellent position to prevent sperm from ascending the cervical os (opening). Although previously not widely recognized, delivering an agent to the non-cervical regions of the vagina (in addition to the cervical region) is also important. When the goal is contraception, spermicide delivered on the vaginal side of a cervical barrier device will be positioned at the site where semen is deposited during intercourse. Thus, the semen will be directly exposed to and mixed with the spermicide. This result will speed the inactivation of sperm. The increased speed of sperm inactivation will provide more reliable contraception and might also allow the user the convenience of being able to remove the device sooner after intercourse.

When the goal is the prevention of sexually transmitted diseases (STD), adequate delivery and distribution of the agent, e.g., a microbicide, to the non-cervical region of the vagina is even more beneficial. While some STD pathogens must contact or ascend the cervix to cause disease, many others can directly infect the cells of the entire vaginal surface, for example, Herpes Simplex Virus, *Haemophilus ducreyi*, *Treponema pallidum*, Human Papillomavirus and Human Immunodeficiency Virus. Reliable prevention of these infections requires coating the mucosa of the entire vagina with the protective agent, not just delivering the agent to the cervical region covered by the barrier device. Finally, when the goal is treatment of an established condition, it is again beneficial to coat all regions of the vagina with the treating agent.

These considerations are even more important when it is necessary or desirable to deliver a relatively large volume of agent to all regions of the vagina. One reason that this may be necessary or beneficial is the need to assure wide distribution and complete coverage of all regions of the vagina in order to provide effective treatment or prevention to all areas. The surface of the vagina has many small folds (rugae) and increasing the delivered volume aids in assuring coverage of all these folded surfaces. A second reason is to deliver an agent with limited potency, which requires that the device deliver a large volume to achieve an effective dose. Moreover, if a large volume is employed, it is advantageous to have a means of removing this large volume after its use in order to avoid absorption or discharge of the agent from the vaginal introitus.

The present invention is a vaginal device that can be preloaded with an agent and sealed in a package specifically designed to be used with the device. The invention also provides a means to deliver and distribute a substantial volume of an agent to all regions of the vagina. It also provides an efficient means of removing most of the agent along with the device when it is removed from the vagina after use.

SUMMARY OF THE INVENTION

The present invention discloses a device, a kit and a method for simultaneously delivering at least one beneficial agent to both the cervical and vaginal lumen sides of a vagina. The device is made of a) a flexible circular rim having an inner rim surface, an outer rim surface and a cross-sectional profile with a rim height greater than the rim width and b) a flexible dome having a multiply-folded surface (akin to a hat such as a sombrero). The device exists in either a relaxed state or in a laterally compressed state. In the compressed state, the multiple folds in the dome form at least one pouch above the rim and at least two pouches below the rim.

In a preferred embodiment, the cross-sectional profile of the rim is greater than about 1.5:1 (height:width). In a more preferred embodiment, the cross-sectional profile of the rim is less than 12 mm in height. In a most preferred embodiment, the cross-sectional profile of the rim is less than or equal to 8 mm in height.

In another preferred embodiment, the inner rim surface is shaped to facilitate stable contact with an opposing inner rim surface when pressure is applied laterally to compress the rim. In a more preferred embodiment, a pressure of between about 300 and 1000 grams compressive-force is required to be applied to the opposing outer rim surfaces to form a stable contact with the opposing inner rim surfaces. In another preferred embodiment, the outer rim surface comprises at least one groove that reduces the tendency of the compressed device to slip between the fingers and that enhances the seal between the outer rim surface and the vaginal wall.

The kit for simultaneously delivering at least one beneficial agent to both cervical and vaginal lumen sides of a vagina is made of a) a device having a flexible circular rim having an inner rim surface, an outer rim surface and a cross-sectional profile with a rim height greater than the rim width and a flexible dome having a multiply folded "sombrero" shape, b) a package having a flat bottom for holding the device and the beneficial agent and space for elongation of the device that occurs when the rim is compressed, and at least one beneficial agent. The device exists in either a relaxed state or in a compressed state. When the rim is compressed laterally, the dome forms a single pouch above the rim and two pouches below the rim.

In a preferred embodiment, the cross-sectional profile of the rim is greater than about 1.5:1 (height:width). In a more preferred embodiment, the cross-sectional profile of the rim is less than 12 mm in height. In a most preferred embodiment, the cross-sectional profile of the rim is less than or equal to 8 mm in height.

In another preferred embodiment, the inner rim surface is shaped to facilitate stable contact with an opposing inner rim surface when pressure is applied to opposing outer rim surfaces. In a more preferred embodiment, a pressure of between about 300 and 1000 grams compressive-force is required to be applied to the opposing outer rim surfaces to form a stable contact with the opposing inner rim surfaces. In another preferred embodiment, the outer rim surface comprises at least one groove that reduces the tendency of the compressed device to slip between the fingers and that enhances the seal between the outer rim surface and the vaginal wall.

In another preferred embodiment of the kit, the beneficial agent is selected from the group consisting of spermicides, bactericides, viricides, fungicides, protozoacides, hormones, nucleic acids, proteins, enzymes, vaccinogens, antibodies or cytokines, peptides, metal chelators and buffers.

The method for simultaneously delivering at least one beneficial agent to both cervical and vaginal lumen sides of a vagina, comprising inserting a device into a vagina. The device is made of a flexible circular rim having an inner rim surface, an outer rim surface and a cross-sectional profile with a rim height greater than the rim width and a flexible dome having a multiply-folded surface (akin to a hat such as a sombrero). The device exists in either a relaxed (circular) state or in a compressed state. In the compressed state, the multiple folds in the dome form one pouch above the rim and two pouches below the rim. The pouches contain at least one beneficial agent.

In a preferred embodiment, the cross-sectional profile of the rim is greater than about 1.5:1 (height:width). In a more preferred embodiment, the cross-sectional profile of the rim is less than 12 mm in height. In a most preferred embodiment, the cross-sectional profile of the rim is less than or equal to 8 mm in height.

In another preferred embodiment, the inner rim surface is shaped to facilitate stable contact with an opposing inner rim surface when pressure is applied to opposing outer rim surfaces. In a more preferred embodiment, a pressure of between about 300 and 1000 grams compressive-force is required to be applied to the opposing outer rim surfaces to form a stable contact with the opposing inner rim surfaces. In another preferred embodiment, the outer rim surface comprises at least one groove that reduces the tendency of the compressed device to slip between the fingers and that enhances the seal between the outer rim surface and the vaginal wall.

In another preferred embodiment of the method, the beneficial agent is selected from the group consisting of spermicides, bactericides, viricides, fungicides, protozoacides, hormones, nucleic acids, proteins, enzymes, vaccinogens, antibodies or cytokines, peptides, metal chelators and buffers.

BRIEF DESCRIPTION OF THE DRAWINGS

FIGS. 3A and 3B show the device (11) of the present invention in the open or relaxed (FIG. 3A) and in the compressed forms (FIG. 3B), thereby revealing the formation of pouches (12) of dome (13) material formed and held above and below the plane of the rim (14) by lateral compression of the rim (14).

FIGS. 4A-D show partial cross-sectional views of rim shapes that form a stable contact when the rim (14) is compressed.

FIGS. 5A and 5B show partial cross-sectional views of alternative shapes of the outer surface of the rim (14).

FIGS. 6A-D shows top-down (FIGS. 6A and 6C) and cross-sectional views (FIGS. 6B and 6D) of the device (11) of the present invention in its package (15), thereby revealing the device (11) held without lateral compression (FIGS. 6A and 6B) and an alternative package shape that holds the device (11) in partial compression (FIGS. 6C and 6D).

FIGS. 7A shows a side view of compressed rim (14) held above package tray (16) to reveal that lateral compression induces a slight downward arcing of the rim (14) due to the elastic constraints of the dome. FIG. 7B shows that the rim (14) is then pressed downward, forcing the arced-rim flat against the flat bottom of the tray (16). The downward arcing of the ends increases the downward force at these ends, thus equalizing the force along the entire rim and more efficiently removing agent from the tray bottom.

DETAILED DESCRIPTION OF THE PREFERRED EMBODIMENT

Figure 1:
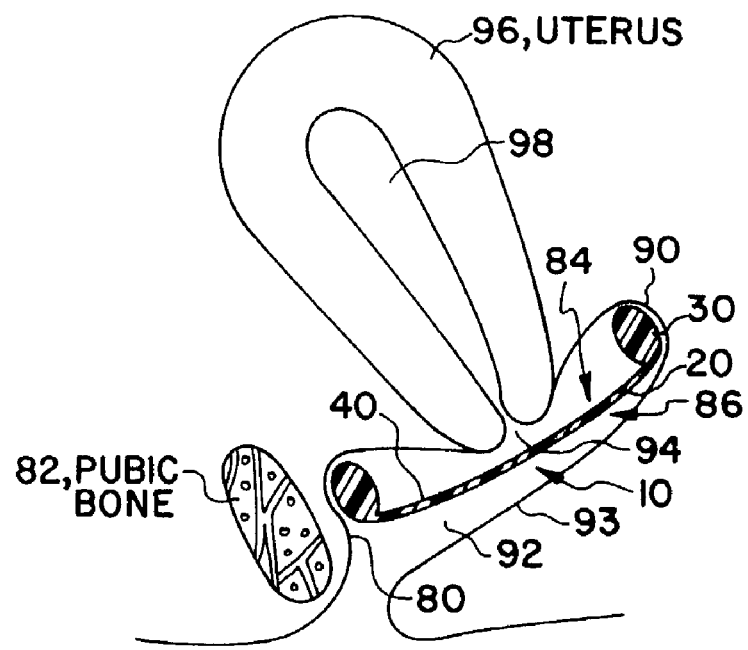
FIG. 1 is a cross-sectional view of a conventional contraceptive diaphragm (10) in place in upper vagina (92), residing anteriorly on the "ledge" (80) formed by the pubic bone (82) and extending posteriorly well into the vaginal formix (90). The vaginal lumen (92), vaginal wall (93), uterine cervix (94), uterus (96) and uterine cavity (98) are also shown in this cross-sectional view. The cervical (84) and non-cervical sides (86) of the diaphragm (10) are also shown.
Figure 2:
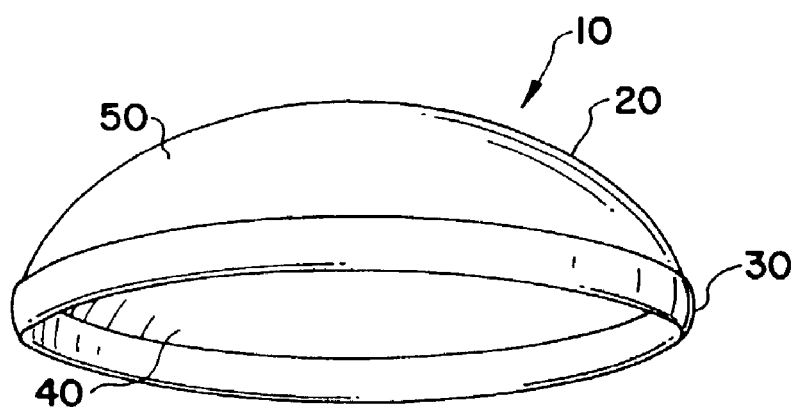
FIG. 2 shows a conventional contraceptive diaphragm (10) having a thin and flexible dome (20) attached at its margin to a flexible circular rim (30). The inner or concave surface (40) and outer or convex surface (50) of the dome (20) are also shown.

The present invention discloses a device, a kit and a method for simultaneously delivering at least one beneficial agent to both the cervical and vaginal lumen sides of a vagina. The device is made of a flexible circular rim and a flexible dome. The device can exist in either a relaxed state or in a compressed state. In the compressed state, three pouches are formed for carrying and delivering of the beneficial agent to both the cervical and vaginal lumen sides of the vagina.

DEVICE: The device (11) comprises a flexible circular rim (14) with a flexible dome (13) attached at its margin to the rim. A beneficial agent is applied to both surfaces of the dome. The device delivers a large volume of agent to all regions of the vagina by preventing wipe-off of the agent from both sides of the device during insertion. Prevention of wipe-off at the vaginal introitus is achieved by shaping and positioning the dome so that it forms pouches by folding above and below the rim as the rim is compressed in preparation for vaginal insertion (see FIGS. 3A and 3B). The agent sequestered in these pouches is not wiped off during insertion regardless of the tone of the circumvaginal sphincter. Not only does this assure delivery of the desired dose, it reduces the waste and resulting messiness of agent accumulating at the introitus and on the fingers. Finally, the device not only prevents wipe-off of the agent during insertion but since the rim expands when the device is inside the vagina, the design spreads the agent to both cervical and non-cervical regions of the vagina. Since the rim expands upon being inserted, the agent is not permanently sequestered in an inaccessible fold or cul-de-sac.

When the device is removed, it is advantageous if the device will remove as much of the "spent" or used up agent as possible, so that it will not be absorbed or exit the vagina as a vaginal discharge. With a contraceptive product, it is also useful if the device can remove as much semen as possible from the vagina when the device is removed postcoitally. This again reduces vaginal discharge and can reduce the risk of conception or transmission of STD pathogens contained in the semen. This desirable effect can be enhanced by employing a rim cross-sectional profile with an elongated aspect ratio, that is, one with a height greater than its width (see FIGS. 3A-3B, 4A-4D and 5A-5B). The elongated aspect ratio of the rim provides a spatula or squeegee-like effect which gently wipes the agent and semen from the vaginal mucosa as the device is withdrawn.

Another advantage of elongating the cross-sectional profile in the vertical dimension is to reduce the tendency of the rim to arc (downward from the plane of the rim) during compression. O-rings and similarly many contraceptive diaphragms with rims that have a circular cross-sectional profile, arc dramatically when compressed laterally along a diameter of their ring shape. This extreme arcing makes them poorly suited for use with the package described below. An elongated profile, greater than about 1.5:1 (height: width) shows a reduced tendency to arc in comparison with a circular cross-sectional profile. To avoid excessive arcing, it is also necessary to shape the attached dome with sufficient slack to prevent stretching of the dome from inducing the rim to arc.

It is advantageous to shape the inner rim surface so that the opposing rim surfaces that come together as the device is compressed form a stable contact, unlike the unstable configuration that occurs when compressing a rim with a circular cross-section. Several shapes that will achieve a stable contact are illustrated in FIGS. 4A-4D. These configurations prevent the rim from twisting into a "figure-8" shape and allow a more secure grip on the device. The height of this cross-sectional profile should not exceed 12 mm, preferably not exceed 8 mm, since otherwise, the device protrudes excessively into the vaginal barrel and is more likely to obstruct and be felt by the penis during intercourse.

The outer rim surface should be shaped to avoid any sharp edges. However, it may be advantageous to provide one or more shallow grooves (17) in the outer surface of the rim (14), as shown in the examples drawn in FIGS. 5A and 5B. This provides a more secure grip to the fingers as the device is lifted out of the package. This gentle texturing also helps to hold the anterior edge of the device from slipping down from its stable position in the vagina at the "pubic ledge" (see FIG. 1).

The entire device can be fabricated by injection molding using methods obvious to those skilled in the art. A metal spring can be incorporated into the rim during molding, as in conventional diaphragms. Alternatively, the metal spring can be omitted and the intrinsic resilience of the material forming the rim can be relied on to provide the requisite degree of stiffness to allow insertion into and retention by the vagina. Or, the rim can be injection molded separately and the flexible dome attached by thermal, ultrasonic or radio-frequency welding to the rim. A pre-shaped dome can be thus attached or a flat film can be attached and subsequently shaped by vacuum thermoforming by methods well known in the art. The device has the beneficial attribute that it will deliver large quantities of an agent to all regions of the vagina even if it is mistakingly inserted upside down.

The materials for the rim and dome can be chosen from many materials obvious to those skilled in the art. These materials include but are not limited to polyurethane, silicone, polyethylene, styrene-ethylene-butylene-styrene block copolymer (Krayton®) or ethylene vinyl acetate. These and other materials can be used alone or in combination and as multilayer laminates or as mixtures. The stiffness required can be adjusted, by choice of materials and material dimensions, according to factors such as ease of insertion, comfort and reliable retention within the vagina during wear before and during intercourse, and ease of removal. Experience with contraceptive diaphragms suggests that the stiffness should be between 300 and 1000 grams compressive-force required to compress the rim sides together.

PACKAGE: The package (15) used with the device (11) is shaped to allow efficient retention of the agent by both sides of the device as the device is compressed and lifted from the package (see FIGS. 6A and 6B). Crucial elements for the package are a substantially flat bottom to allow the agent to be scooped up by the "squeegee action" of the device rim and sufficient room for the elongation of the device that occurs when the rim is compressed. This allows the device to be compressed before lifting it from the package. This in turn is also advantageous in trapping the dome in the folded configuration that prevents wipe-off of agent from both sides of the dome.

The package holds the agent in place during shipment and storage in the proper locations that will allow efficient vaginal delivery. The package also prevents the agent from coating the outer portion of the rim contacted by the fingers. The presence of agent on the rim might interfere with the handling of the device by making it slippery. Finally, the package is configured in a way that guides the user in compressing the device and picking it up in a orientation that allows for easy and efficient vaginal insertion. For example, finger detentes on the package can be used to guide the user to compress the device at the intended place. FIGS. 6A and 6B show the device (11) in its package (15).

When used, the preloaded device-package combination is opened by removing the top, for example, by stripping back a foil-laminate film, to expose the device (11) laying in the lower tray-like packaging piece (16). The index finger and thumb are placed in the detentes. The rim is pushed downward to keep it in close contact with the bottom of the tray and then the two opposing sides of the rim are compressed inward. As the rim is compressed, its bottom edge wipes up most of the agent from the bottom of the tray.

A small amount of arcing of the rim during compression (toward the lower edge of the rim that presses against the lower tray-like packaging piece) aids the process of loading agent into the device from the package (see FIGS. 7A). Mild arcing in this direction increases the force with which the ends of the compressed rim press against the bottom of the package tray. This improves the force distribution along the bottom of the rim, making it more nearly equal from the center (where the fingers are pressing it down) out toward the tips (see FIG. 7B). This is analogous to the way camber in alpine skis (arcing downward toward each end) is used to apply more force to the tips and tails of the skis than if the skis were flat. The result in both cases is a more even force distribution along the entire length of the bottom of the compressed device.

Pressing the rim downward before and during the rim compression also ensures that the central upward-projecting portion of the dome will be trapped (FIG. 3B) within the opposed sides of the rim brought together by the lateral compressing movement. This holds this portion of the dome in the upper pouch that will prevent wipe-off of the agent from the inner surface of this upper pouch during vaginal insertion.

The cavity in the package tray element can be shaped in an oval that will hold the device partially compressed. This has the advantage of reducing the overall volume of the package since less empty space is enclosed by the package (see FIG. 6B). This reduces the amount of dead-space inside the package. (Dead-space increases the amount of air sealed in the package and may reduce the shelf-life of the beneficial agent.) Using a more narrow oval tray cavity also reduces the span over which the flexible top packaging piece must be stretched and thus can reduce the thickness of material that must be employed for this piece. Finally, the narrower oval improves the visual appeal and handling ease of the package since bulkiness is reduced, and the positions at which to laterally compress (squeeze) the device are more obvious.

Most of any agent that is adherent to the top member of the package can be transferred downward onto the device by the following maneuver. The bottom of the package is struck forcefully against a hard surface or against ones other hand before opening the package. The sudden deceleration of the package and its contents causes most of any agent adherent to the top member to move downward onto the device.

Thus, this device-package combination provides a simple and efficient means of transferring most of any agent adherent to either the top or the bottom package component to the device in preparation for insertion into the vagina. This not only minimizes waste but improves reproducibility in applying a specific chosen dose of the agent.

The following examples are intended to illustrate the present invention more practically but not to limit it in any way.

EXAMPLE 1

Example 1 tests the ability of a preferred embodiment of the present invention (designated RPTcup, with a rim height of 8 mm, rim width of 4 mm, and a dome shape as illustrated in FIG. 3) to deliver a beneficial agent (BufferGel™, an aqueous vaginal contraceptive and microbicidal gel, U.S. Pat. No. 5,617,877) after preloading the agent on the vaginal lumen side of the device. The agent was loaded into the large pod projecting through the plane of the rim, the rim was compressed around the agent, and the compressed device was inserted into an artificial vagina.

The artificial vagina was designed to mimic the human vagina's internal pressure, and the constriction at the opening of the vagina provided by the introital sphincter. It consists of a water-filled tank with a 1.25 inch inside diameter hollow cylinder mounted horizontally in a hole on one side of the tank to mimic the vaginal introitus. A female condom (Reality®, Female Health Company) was attached to the cylinder, projecting into the tank, mimicking the vagina with its flexible wall. To serve as a constriction that mimics the introital (circumvaginal) sphincter, an elastic band was placed around the female condom near the attachment site on the cylinder. The tank was filled with water to a depth 4 cm above the center of the cylinder. The water pressure mimics compression on the vaginal walls caused by the woman's intrabdominal pressure.

The amount of gel delivered was determined by collecting and weighing all gel that failed to enter the artificial vagina (gel left on the inserting fingers, and at the opening of the artificial vagina). The weight of this non-inserted gel was subtracted from the weight of gel that had been loaded on the device to calculate the amount of gel delivered to the interior. The data in Table 1 were generated as described above, and each value shown is the mean value of three replicate determinations.

TABLE 1

| Device Used | Gel Loaded | Gel Delivered | Gel Wasted |
| --- | --- | --- | --- |
| RPTcup | 7.2 grams | 6.8 grams | 0.4 grams |

Thus, Table 1 shows that when loaded with 7.2 grams of gel on the vaginal lumen side, RPTcup delivers 6.8 grams, and wastes (fails to deliver) only 0.4 grams.

EXAMPLE 2

Example 2 tests the ability of RPTcup to deliver gel loaded simultaneously on both its vaginal lumen side and cervical side. Equal quantities of BufferGel™ were loaded on each side of the device, either approximately 5 grams or approximately 7 grams on a side. Delivery to the artificial vagina was tested as described in Example 1. The data in Table 2 were generated as described above and each value shown is the mean value of three replicate determinations.

TABLE 2

| Device Used | Gel Loaded | Gel Delivered | Gel Wasted |
|---|---|---|---|
| RPTcup | 10.04 grams | 9.90 grams | 0.14 grams |
| RPTcup | 14.05 grams | 13.95 grams | 0.10 grams |

Thus, Table 2 shows that RPTcup efficiently delivers gel loaded on both sides, with minimal waste.

EXAMPLE 3

Example 3 tests the ability of the combination of RPTcup and its package (15) to make it possible to deliver a beneficial agent (BufferGel™) on the vaginal lumen side when using a preloaded-device supplied in a package. The agent was loaded onto the vaginal lumen side of the device as in Example 1, and now both device and agent loaded into the package (15).

The device rim was pushed downward to keep it in close contact with the bottom of the tray, and then the rim was compressed laterally inward. As the rim was compressed, its bottom edge wiped up the agent from the bottom of the tray. The device and the agent it contained were lifted free of the package (15), and inserted into an artificial vagina as in Example 1.

The amount of gel delivered was determined by collecting and weighing all gel that failed to enter the artificial vagina (gel left on the package, on the inserting fingers, and at the opening of the artificial vagina). The weight of this non-inserted gel was subtracted from the weight of gel that had been loaded on the device to calculate the amount of gel delivered to the interior of the artificial vagina.

Two other contraceptive diaphragms (Ortho ALL-FLEX®-70, Ortho Pharmaceutical, and Semina-70, Semina Industria e Comercio Ltda.) were tested in the same fashion for their ability to deliver gel on their vaginal lumen (convex) side when loaded with gel into the package (15). The data in Table 3 were generated as described above, and each value shown is the mean value of three replicate determinations.

TABLE 3

| Device Used | Gel Loaded | Gel Delivered | Gel Wasted |
|---|---|---|---|
| Ortho ALL FLEX-70 | 7.1 grams | 2.9 grams | 4.2 grams |
| Semina (70 mm) | 7.0 grams | 4.0 grams | 3.0 grams |
| RPTcup | 7.1 grams | 6.0 grams | 1.1 grams |

Table 3 thus shows that when loaded with 7.1 grams of gel, RPTcup as packaged in the kit delivers 6 grams of gel, and wastes only 1.1 grams of the gel. In contrast, conventional diaphragms (that do not allow efficient "squeegee action" to remove gel from the bottom of the package) deliver substantially less gel, and waste substantially more.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A device for delivering at least one beneficial agent to a vagina on both cervical and vaginal lumen sides of the device, said device comprising:
   a) a flexible rim having a rim circumference and a rim thickness;
   b) a shaped film having a film thickness less than the rim thickness through at least a substantial portion of said rim circumference, said film including an outer region projecting below the rim and an inner region projecting above the rim; and
   c) a beneficial agent contacting said inner region of said film and a beneficial agent contacting said outer region of said film, wherein the agent is substantially sequestered in at least one pouch formed by said inner region and at least one pouch formed by said outer region when the film is in a compressed state, and wherein the agent is substantially distributed from both said inner region and said outer region when the film is in an expanded state.

2. The device of claim 1, wherein an inner rim surface is shaped to facilitate a stable configuration of said device when pressure is applied to opposing outer rim surfaces.

3. The device of claim 2, wherein a pressure of between about 300 and 1000 grams compressive-force applied to opposing outer rim surfaces is sufficient to bring together opposing inner rim surfaces.

4. The device of claim 1, wherein a cross-sectional profile of the flexible circular rim is less than 12 mm in height.

5. The device of claim 1, wherein a cross-sectional profile of the flexible circular rim is less than or equal to 8 mm in height.

6. The device of claim 1, wherein an outer rim surface comprises at least one groove.

7. The device of claim 1, wherein the beneficial agent associated with the inner region and the beneficial agent associated with the outer region are the same agent.

8. The device of claim 1, wherein the film is shaped as a dome.

9. A kit for delivering at least one beneficial agent to a vagina, comprising:
   a) a device comprising
      i) a flexible rim; and
      ii) a shaped film having an outer region projecting below the rim and an inner region projecting above the rim, wherein said inner region and said outer region of the film exist in either an expanded state or in a compressed state and wherein the film forms at least a single pouch above the rim and at least a single pouch below the rim when the film is in the compressed state;
   b) at least one beneficial agent contacting said inner region of the film and at least one beneficial agent contacting said outer region of the film; and
   c) a package for holding the device and the beneficial agent, wherein said package is shaped to allow substantial retention of said agent in said inner region and said outer region of the film when the film is in a compressed state within the package and wherein said package includes space for elongation of the device when the device is in the compressed state within the package.

10. The kit of claim 9, wherein an inner rim surface is shaped to facilitate a stable configuration of said device when pressure is applied to opposing outer rim surfaces.

11. The kit of claim 10, wherein a pressure of between about 300 and 1000 grams compressive-force applied to opposing outer rim surfaces is sufficient to bring together opposing inner rim surfaces.

12. The kit of claim 9, wherein a cross-sectional profile of the rim is less than 12 mm in height.

13. The kit of claim 8, wherein a cross-sectional profile of the rim is less than or equal to 8 mm in height.

14. The kit of claim 9, wherein an outer rim surface comprises at least one groove.

15. The kit of claim 9, wherein the beneficial agent is selected from the group consisting of spermicides, bactericides, viricides, fungicides, protozoacides, hormones, nucleic acids, proteins, enzymes, vaccinogens, antibodies or cytokines, peptides, metal chelators and buffers.

16. The device of claim 9, wherein the beneficial agent associated with the inner region and the beneficial agent associated with the outer region are the same agent.

17. The device of claim 9, wherein the film is shaped as a dome.

18. A method for delivering at least one beneficial agent to a vagina, comprising:
   a) placing a beneficial agent in contact with an inner region and an outer region of a shaped film of a device including a flexible rim having an outer rim surface, wherein said inner region proiects above the rim and wherein said outer region projects below the rim;
   b) applying pressure to opposing outer rim surfaces to form a compressed state of the device, wherein said inner region and said outer region each form at least one pouch to substantially sequester the agent in said inner region and said outer region said compressed state;
   c) inserting the device into the vagina in said compressed state;
   d) releasing pressure from opposing outer rim surfaces to allow said inner region pouch and said outer region pouch to expand to substantially distribute the agent to the vagina from both said inner region and said outer region.

19. The method of claim 18, wherein an inner rim surface is shaped to facilitate a stable configuration of said device when pressure is applied to opposing outer rim surfaces.

20. The method of claim 19, wherein a pressure of between about 300 and 1000 grams compressive-force applied to opposing outer rim surfaces is sufficient to bring together opposing inner rim surfaces.

21. The method of claim 18, wherein a cross-sectional profile of the rim is less than 12 mm in height.

22. The method of claim 18, wherein a cross-sectional profile of the rim is less than or equal to 8 mm in height.

23. The method of claim 18, wherein an outer rim surface comprises at least one groove.

24. The method of claim 18, wherein the beneficial agent is selected from the group consisting of spermicides, bactericides, viricides, fungicides, protozoacides, hormones, nucleic acids, proteins, enzymes, vaccinogens, antibodies or cytokines, peptides, metal chelators and buffers.

25. The method of claim 18, wherein the beneficial agent associated with the inner region and the beneficial agent associated with the outer region are the same agent.

26. The device of claim 18, wherein the film is shaped as a dome.

27. A device for distributing at least one beneficial agent to a vagina on both cervical and vaginal lumen sides of the device, said device comprising:
   a) a flexible rim;
   b) a shaped film including at least one outer region and at least one inner region, the outer region projecting below the rim and the inner region projecting above the rim; and
   c) a beneficial agent contacting said inner region of said film and a beneficial agent contacting said outer region of said film, wherein at least a portion of the agent is sequestered in at least one pouch formed by said inner region and at least one pouch formed by said outer region when the film is in a compressed state and wherein a substantial portion of the sequestered agent is not sequestered when the film is in an expanded state.

28. The device of claim 27, wherein the compressed state includes an inner rim surface of the rim compressed together with an opposing inner rim surface of said rim.

29. The device of claim 28, wherein the inner rim surface of the rim is compressed together with the opposing inner rim surface of said rim when a pressure of between about 300 and about 1000 grams compressive-force is applied to opposing outer rim surfaces.

30. The device of claim 27, wherein an inner surface of the rim is shaped to facilitate a stable configuration of said device in the compressed state.

31. The device of claim 27, wherein an outer rim surface comprises at least one groove.

32. The device of claim 27, wherein the beneficial agent is selected from the group consisting of spermicides, bactericides, viricides, fungicides, protozoacides, hormones, nucleic acids, proteins, enzymes, vaccinogens, antibodies or cytokines, peptides, metal chelators and buffers.

33. The device of claim 27, wherein the beneficial agent associated with the inner region and the beneficial agent associated with the outer region are the same agent.

34. The device of claim 27, wherein the film is shaped as a dome.

35. A method for delivering at least one beneficial agent to a vagina, comprising:
   providing a device including a flexible rim and a shaped film, wherein said film includes at least one outer region and at least one inner region;
   contacting said inner region of said film with a beneficial agent and contacting said outer region of said film with a beneficial agent, wherein at least a portion of the agent is sequestered in at least one pouch formed by said inner region and at least one pouch formed by said outer region when the rim is in a compressed state, and wherein a substantial portion of the sequestered agent is not sequestered when the rim is in an expanded state; and
   inserting the device into the vagina.

36. The method of claim 35, wherein the beneficial agent associated with the inner region and the beneficial agent associated with the outer region are the same agent.

37. The method of claim 35, wherein the inner region and the outer region of the film form pouches when the rim is in a compressed state.

38. The method of claim 37, wherein at least one pouch forms above the rim and at least one pouch forms below the rim.

39. The method of claim 35, wherein the film is shaped as a dome.

* * * * *